United States Patent
Elgaard et al.

(10) Patent No.: US 10,052,151 B2
(45) Date of Patent: Aug. 21, 2018

(54) APPARATUS AND METHOD FOR OCCLUDING A VESSEL BY RF EMBOLIZATION

(71) Applicant: COOK MEDICAL TECHNOLOGIES LLC, Bloomington, IN (US)

(72) Inventors: Per Elgaard, Haslev (DK); Allan Torp, Bjaeverskov (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 561 days.

(21) Appl. No.: 14/681,644

(22) Filed: Apr. 8, 2015

(65) Prior Publication Data
US 2015/0289930 A1    Oct. 15, 2015

(30) Foreign Application Priority Data

Apr. 10, 2014 (GB) .................................. 1406496.8

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 2017/00075* (2013.01);
(Continued)

(58) Field of Classification Search
CPC ............ A61B 18/1206; A61B 18/1492; A61B 2018/00404; A61B 2018/00416;
(Continued)

(56) References Cited

U.S. PATENT DOCUMENTS

| 5,057,105 A | 10/1991 | Malone et al. |
| 5,437,664 A * | 8/1995 | Cohen ................ A61B 18/1492 606/34 |

(Continued)

FOREIGN PATENT DOCUMENTS

| EP | 2 662 041 A2 | 11/2013 |
| EP | 2 939 629 A2 | 11/2015 |

(Continued)

OTHER PUBLICATIONS

Search and Examination Report for GB 1513105.5 dated Aug. 5, 2015.

(Continued)

*Primary Examiner* — Michael Peffley
(74) *Attorney, Agent, or Firm* — Brinks Gilson & Lione (57) ABSTRACT

An RF ablation system includes an electrode element of elongate form and a cathode pad. A control unit includes a processing unit, a power unit and, optionally, a temperature sensor and/or an impedance sensor. The control unit in one embodiment carries out RF ablation in at least two phases, the first phase at a higher energy level and a second phase, after at least partial retraction of the anode element, at a second lower phase in order to close any remaining lumen within a blood clot formed within the vessel during the first phase. Other embodiments provide for sensing retraction of the anode terminal and effecting RF ablation during and/or after the retraction process in order to create a more effective occlusion barrier.

24 Claims, 5 Drawing Sheets

(51) Int. Cl.
*A61B 18/00* (2006.01)
*A61B 17/00* (2006.01)

(52) U.S. Cl.
CPC ............... *A61B 2018/0063* (2013.01); *A61B 2018/00404* (2013.01); *A61B 2018/00416* (2013.01); *A61B 2018/00589* (2013.01); *A61B 2018/00654* (2013.01); *A61B 2018/00666* (2013.01); *A61B 2018/00702* (2013.01); *A61B 2018/00791* (2013.01); *A61B 2018/00875* (2013.01); *A61B 2018/00898* (2013.01); *A61B 2018/1467* (2013.01)

(58) Field of Classification Search
CPC .. A61B 2018/00589; A61B 2018/0063; A61B 2018/00654; A61B 2018/00666; A61B 2018/00702; A61B 2018/00791; A61B 2018/1467

See application file for complete search history.

(56) References Cited

U.S. PATENT DOCUMENTS

| | | | |
|---|---|---|---|
| 5,556,396 A | 9/1996 | Cohen et al. | |
| 5,709,224 A | 1/1998 | Behl et al. | |
| 5,743,905 A | 4/1998 | Eder et al. | |
| 5,827,271 A * | 10/1998 | Buysse | A61B 18/1206 606/34 |
| 6,019,757 A | 2/2000 | Scheldrup | |
| 6,066,139 A | 5/2000 | Ryan et al. | |
| 6,142,992 A * | 11/2000 | Cheng | A61B 18/1206 606/34 |
| 6,264,650 B1 | 7/2001 | Hovda et al. | |
| 6,270,495 B1 | 8/2001 | Palermo | |
| 6,327,505 B1 * | 12/2001 | Medhkour | A61N 1/3702 604/114 |
| 6,398,779 B1 | 6/2002 | Buysse et al. | |
| 6,539,265 B2 | 3/2003 | Medhkour et al. | |
| 6,676,657 B2 | 1/2004 | Wood | |
| 8,636,729 B2 * | 1/2014 | Esch | A61B 18/08 606/28 |
| 8,936,631 B2 * | 1/2015 | Nguyen | A61N 1/403 606/29 |
| 2001/0016739 A1 | 8/2001 | Goldman et al. | |
| 2001/0020167 A1 | 9/2001 | Woloszko et al. | |
| 2003/0199864 A1 | 10/2003 | Eick | |
| 2004/0199151 A1 | 10/2004 | Neuberger | |
| 2004/0199156 A1 | 10/2004 | Rioux et al. | |
| 2006/0142824 A1 * | 6/2006 | Zikorus | A61B 18/1206 607/96 |
| 2006/0293649 A1 | 12/2006 | Lorang et al. | |
| 2008/0065058 A1 | 3/2008 | Neuberger | |
| 2008/0281315 A1 | 11/2008 | Gines | |
| 2009/0248007 A1 | 10/2009 | Falkenstein et al. | |
| 2010/0030212 A1 | 2/2010 | Aramayo | |
| 2010/0106150 A1 | 4/2010 | Thompson et al. | |
| 2010/0268217 A1 | 10/2010 | Habib | |
| 2011/0144657 A1 | 6/2011 | Fish et al. | |
| 2012/0071873 A1 * | 3/2012 | Thompson | A61B 18/08 606/41 |
| 2014/0378970 A1 | 12/2014 | Thompson | |

FOREIGN PATENT DOCUMENTS

| | | |
|---|---|---|
| GB | 2485191 A | 5/2012 |
| WO | WO 2006/054170 A1 | 5/2006 |
| WO | WO 2006/068313 A1 | 6/2006 |
| WO | WO 2006/069313 A1 | 6/2006 |
| WO | WO/2010/080974 | 7/2010 |

OTHER PUBLICATIONS

Search and Examination Report for GB1406496.8 dated Apr. 27, 2015.
Extended European Search Report for EP 16275138.2-1659/3155122, dated May 18, 2017.
Search and Examination Report for GB 1517822.1, dated Jun. 2, 2016.
GB Combined Search and Examination Report for GB 1517822.1, dated Apr. 6, 2016.
Extended European Search Report for EP15275109.5-1659/2939629, dated Jan. 25, 2016.
Examination Report for GB 1517822.1, dated Aug. 26, 2016.
European Search Report for EP 15 27 5109, dated Jan. 19, 2016.

* cited by examiner

APPARATUS AND METHOD FOR OCCLUDING A VESSEL BY RF EMBOLIZATION

CROSS-REFERENCE TO RELATED APPLICATIONS

This application claims the benefit of priority under 35 U.S.C. § 119(a) to Great Britain Patent Application No. 1406496.8, filed Apr. 10, 2014, which is incorporated by reference here in its entirety.

TECHNICAL FIELD

The present invention relates to apparatus and a method for occluding or closing a vessel by means of RF embolization.

BACKGROUND ART

There are numerous medical conditions when it is desired or necessary to close a body vessel, including for instance in the treatment of aneurysms, arteriovenous malformations, arteriovenous fistulas, for starving organs of oxygen and nutrients for instance in the treatment or containment of cancerous growths, and so on.

Several techniques are known and in use for closing or occluding such body vessels. Traditionally, vessels have been closed by means of external ligation, which generally must be carried out by an open surgery procedure, with its associated risks, inconvenience and long patient recovery times. Other more recent methods aim to use an endoluminal procedure to insert into the vessel or organ one or more occlusion devices, such as a metal framed occluder, pellets or the like, able to obstruct the flow of blood in the vessel.

It is also known to seek to constrict a vessel by endoluminal ablation, causing contraction of the vessel and/or coagulation of blood to form a blood clot in the vessel. A technique which has been considered suitable is RF ablation, in which an electrical terminal is fed endoluminally into the vessel and an electrical pulse at RF frequencies applied to the electrical terminal. The conductivity of blood and/or the vessel tissues causes localised heating. This heating can be used to cause damage to the tissue (intima) of the vessel wall, resulting in vessel contraction. In other devices RF ablation heats the surrounding blood, causing this to coagulate around the electrical terminal and form a blood clot which blocks the vessel.

Two types of RF ablation apparatus are generally contemplated in the art, the first being a monopolar system having an elongate anode terminal and a cathode pad. The anode terminal is designed to be fed endoluminally into the patient's vessel, while the cathode pad is positioned against the person's outer body, as close as practicable to the anode terminal. Electrical energy applied to the anode terminal will pass by conduction through the patient to the cathode pad. There will be localised heating at the anode terminal, which effects the desired ablation.

A problem with monopolar systems is that it can be difficult to control the extent of damage to surrounding tissues and organs, as well as to the vessel wall. This risks damaging the vessel to the point of rupture, as well as possible irreversible damage to neighbouring organs.

Another RF ablation system uses a bipolar arrangement, in which an elongate electrical element includes both the anode and cathode terminals, which are spaced longitudinally from one another at a distal end of the electrical element. Current passes between the anode and the cathode terminals through the surrounding blood, causing localised heating and coagulation of the blood. A bipolar system has been considered to provide more localised heating and therefore reduced risk of damage to surrounding organs and tissue.

A problem particularly with a bipolar system, but also experienced in a monopolar system, lies with the retraction of the electrical terminal from the vessel at the end of the ablation process. In a system which ablates the vessel wall to cause its contraction, the electrical terminal can become attached to the vessel wall tissue, with the risk of tearing and rupturing the vessel wall. In a system which ablates the surrounding blood to generate a blood clot in the vessel, there is the risk that the blood clot is dragged with the electrical element and that the occlusion of the vessel is as a consequence lost. There is also the risk of leaving an opening in blood clot where the electrical terminal resided, which can result in incomplete occlusion and the risk of recanalization.

Some such devices have attempted to address the above problems by having an electrical element with a detachable terminal end. However, this entails leaving a foreign body in the patient.

Examples of prior art devices and methods can, for instance, be found in US-2009/0248007, US-2001/0020167, US-2001/0016739, U.S. Pat. No. 6,539,265, WO-2010/080974, U.S. Pat. Nos. 6,264,650, 6,066,139, 6,676,657, US-2010/0268217, U.S. Pat. Nos. 5,709,224, 6,398,779 6,019,757 and 5,743,905.

SUMMARY OF THE INVENTION

The present invention seeks to provide improved apparatus for occluding or closing a body vessel.

According to an aspect of the present invention, there is provided apparatus for closing a blood vessel including: an elongate electrode element for being passed endoluminally to a treatment site and having at least one electrical terminal at a distal end thereof; a power supply for supplying energy to the electrode element; a detection unit for detecting at least one operational change at the at least one electrical terminal; a control unit connected to the power supply and to the detection unit; wherein the control unit is operable to control the power supply to supply energy to the electrode element at a first power level to cause a primary blood coagulation, to detect at least one operational change at the at least one electrical terminal and to control the power supply to supply energy to the electrode element at a second power level lower than the first power level to cause a secondary blood coagulation once the operational change has been detected.

The apparatus disclosed herein provides for closing any opening or lumen left by the retracting or retracted electrical element, namely by applying energy through the electrical element, at a power level less than the initial ablation power, which has the effect of causing secondary blood coagulation. Preferably, the second power level is insufficient to cause the creation of a further vessel occluding barrier, that is a second barrier which closes off the vessel in its entirety. Specifically, the application of the power at the second level stops once sufficient blood has coagulated to close any aperture left by the retracted or retracting electrical element. The occluding barrier created by application of power at the first power level will therefore form the total length of effective vessel occlusion, thereby making the method also suitable in vessel zones having short treatment sites, such as in locations with adjacent vessel side branches and the like.

Preferably, the apparatus includes a user notification unit coupled to the control unit, the control unit being operable to generate a notification on detection of the operational change in the at least one electrical terminal. The notification unit could be a visual notification, an acoustic notification, a vibratory notification, a combination of any of these, or any other suitable notification.

Preferably, the control unit is operable to command a partial retraction of the electrode element in a proximal direction on detection of the operational change. Partial retraction may leave a part of the electrode tip within the formed clot, thereby to keep any aperture therein closed and to ensure that the second phase of ablation takes place within the blood clot and able to close off the residual lumen.

In an embodiment, the apparatus may include a positioning, or drive, unit coupled to the control unit, the positioning unit being operable to effect the partial retraction of the electrode element in the proximal direction on detection of the operational change. The control unit may be operable to generate a notification to effect said partial retraction of the electrode element.

There may be provided an electrode position sensor coupled to the control unit, wherein the control unit is operable to control the power supply to supply energy to the electrode element at the or a second power level lower than the first power level when partial retraction of the electrode element has been detected.

In some embodiments the control unit may be operable to command the power supply to supply power to the electrode element until the electrode element has been retracted by a predetermined distance. The predetermined distance may be equivalent to a desired length of closure of the vessel. In other words, the system of this embodiment is able to create an occluding barrier of varying length.

The operational change preferably includes at least one of: change in measured impedance and change in temperature.

There may be provided a temperature sensor at the distal end of the electrode element.

In an embodiment, the electrode element includes an anode terminal, the apparatus including a cathode pad. In other words, the system may be a monopolar system.

In another embodiment, the electrode element includes anode and cathode terminals. In other words, the system may be a bipolar system.

According to another aspect of the present invention, there is provided apparatus for closing a blood vessel including: an elongate electrode element having at least one electrical terminal at a distal end thereof; a power supply for supplying energy to the electrode element; a detection unit for detecting at least one operational change at the at least one electrical terminal; a position sensor arranged to detect the position of the distal end of the electrode in a patient; a control unit connected to the power supply, to the detection unit and to the position sensor; wherein the control unit is operable to control the power supply to supply energy to the electrode element at a first power level, to determine movement of the electrode and to apply power to the electrode when the electrode has been deemed to have been moved by a first predetermined distance.

In this aspect, the system monitors for a change in the position of the electrode and applies ablation energy in a manner which can elongate the occlusive barrier which is produced.

In one embodiment, the control unit is operable to apply power to the electrical terminal continuously when in an initial position and while the electrode element is moved by the predetermined distance. In another embodiment, the control unit is operable to apply power to the electrical terminal discontinuously, when in an initial position and after the electrode element has been moved by the predetermined distance.

Preferably, the control unit is operable to apply power to the electrical terminal up to a second distance greater than the first predetermined distance. The second distance may be equivalent to a desired length of closure of the vessel.

Advantageously, the electrical terminal has a conductive length and the first predetermined distance is less than said conductive length.

In an embodiment, the control unit is operable to control the power supply to supply energy to the electrode element at a second power level lower than the first power level once the operational change has been detected. This is not essential though, and in other embodiments the control unit may be operable to apply power at the first power level or near the first power level so as to produce an occlusive barrier of radial dimensions at least as significant as that produced prior to movement of the electrode.

There may be provided a positioning unit coupled to the control unit, the positioning unit being operable to move the electrode element in at least a proximal direction. Such a positioning unit can therefore provide an automated ablation system.

There is also described herein a method of closing a blood vessel by means of apparatus including an elongate electrode element having at least one electrical terminal at a distal end thereof and a power supply for supplying energy to the electrode element; the method including the steps of: supplying energy to the electrode element at a first power level; detecting at least one operational change at the at least one electrical terminal; when said operational change has been detected supplying energy to the electrode element at a second power level lower than the first power level.

The method may include steps appropriate for effecting the functionality disclosed herein.

Other features of the apparatus and method disclosed herein will become apparent from the following specific description of preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There are described below various embodiments of apparatus and methods for effecting RF ablation of a body vessel, in particular a blood vessel. The preferred embodiments are designed to create blood clotting, that is to ablate the blood surrounding the electrical element. This can be achieved by selecting an ablation energy level and an ablation time duration suitable to heat surrounding blood, which in some circumstances can be expected to be less than the energy required to ablate the vessel tunica, although there may be experienced some contraction of the vessel as a result of the heating of the blood. The skilled person will be able to determine suitable ablation parameters from common general knowledge in the art. Moreover, the preferred embodiment uses a thin, that is narrow diameter, electrode which minimises the surface area contact with the vessel wall in circumstances where the distal end of the electrode is not deployed in the centre of the vessel.

It is to be appreciated that the level of power applied through the electrode and the time of application will be dependent upon factors including the size of the vessel, the amount and speed blood flow through the vessel, pulsation and turbulence of blood at the point of ablation, and so on.

Although the preferred embodiment is a monopolar system, it is to be understood that the teachings herein can apply also to a bipolar system.

Figure 1:
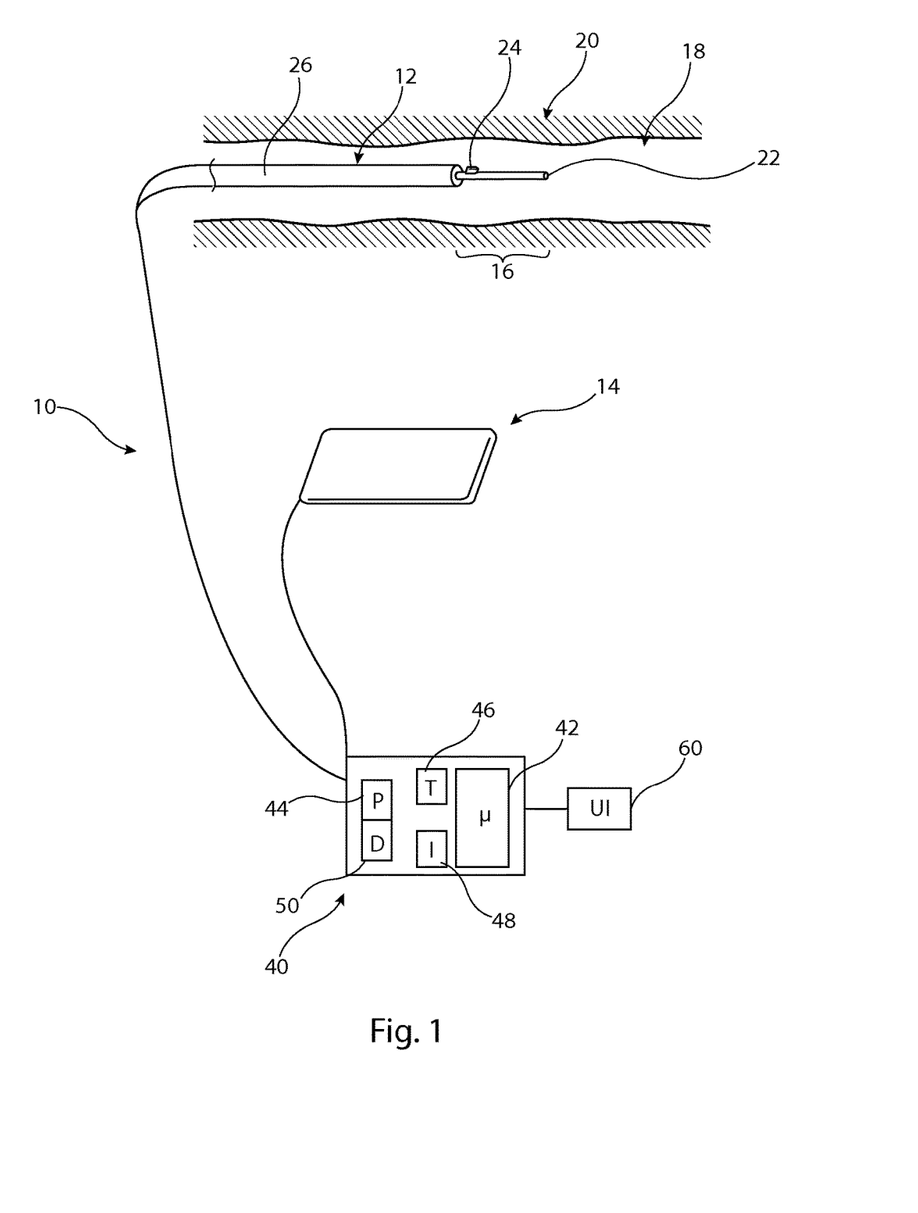
FIG. 1 is a schematic diagram of an embodiment of monopolar RF ablation system.

Referring first to FIG. 1, this shows in schematic form an embodiment of monopolar RF ablation system 10 having an elongate electrode element 12 and a cathode pad 14. The elongate electrode element 12 is designed to be passed endoluminally through the vasculature of a patient up to a treatment site 16 of a vessel 18, that is to the position in a vessel as which it is desired to close or occlude the vessel 18.

The electrode element 12 includes a distal end 20 which in this embodiment has an exposed electrode terminal 22 acting as the anode of the circuit. The electrode element 12 in some embodiments also includes a temperature sensor 24 for measuring temperature at the anode terminal 22, useful in determining the progress of ablation of the vessel.

The electrode element 12 also includes a sheath 26 of electrically insulating material which in practice covers the remainder of the electrode 22, such that a current path in use exists solely from the exposed terminal 22 at the distal end 20 of the electrode element 12.

The electrode element 12 is coupled electrically to a control unit 40, as is the cathode pad 14. As explained below, the control unit 40 is operable to provide energy to the electrode element 12, specifically current at RF frequencies. The anode terminal 22 and cathode pad 14 form a circuit for the RF energy, which will conduct through a patient's body between the anode terminal 22 and the cathode pad 14. It will be appreciated that the cathode pad 14 will be applied against the patient's skin, preferably at a position which is practicably as close as possible to the anode terminal 22, in order to provide this conduction path. There will be localised heating around the anode terminal 22, as a result of its significantly smaller surface area and as a result consequential heating of blood in the vicinity of the anode terminal 22, as explained in further detail below.

The control unit 40 typically includes a processing unit 42, a power delivery circuit 44 coupled to the anode and cathode elements of the system 10, typically one or more sensors including a temperature sensor unit 40 coupled to the temperature probe 24 and/or an impedance sensor unit 48 for measuring impedance between the anode 22 and cathode 14 of the system 10. In some embodiments both of types of sensor units 46 and 48 may be provided.

The control unit 40 may also include an electrode drive unit 50 for moving the electrode 12 within the patient's vessel 18. In some embodiments, the control unit 40 may be provided with a position sensor for measuring the position of the electrode 12 within a patient and in particular for measuring the retraction of the electrode 12 from within the vessel 18. Some embodiments may include both a drive unit 59 and a position sensor.

The processing unit 40 also includes a user interface 60 coupled to the control unit 40 and operable to provide data to a user and for input of user commands to the control unit 40. The user interface 60 may, in its simplest embodiment, include an on/off switch for operating the control unit 40 and therefore the RF ablation, with the control unit 40 then effecting the desired ablation process under the command of the unit 40 solely. In other embodiments, the user interface 60 may be more sophisticated and enable, for example, a user to select different modes of ablation and also to produce, for instance, occluding barriers of different lengths, as described in further detail below.

The user interface 60 preferably also includes an output for providing ablation feedback and/or warning signals to a user. It may, for example, provide an indication of measured temperature and/or impedance, an indication of progress of ablation of the vessel and so on. For such purposes, the user interface 60 may include a visual unit, for example a display to display quantitative data such as graphs, measures of temperature and impedance, determined length of occlusion and so on. In other embodiments the display may be simpler, having for instance simple visual indicators such as one or more illuminated lamps. The output could also be an acoustic output and/or, as appropriate, a tactile output such as a vibration generator and so on. Any combination of user feedback devices may be provided.

The apparatus 10 of FIG. 1 is intended to cause heating of blood within the vessel 18 so as to occlude the vessel by the formation of a blood clot, rather than by ablation and damage of the tunica (tissues) of the vessel wall. FIGS. 2A to 2D show in schematic form the preferred mode of operation of the apparatus 10 of FIG. 1 and method of ablating a vessel 18.

Figure 2A:
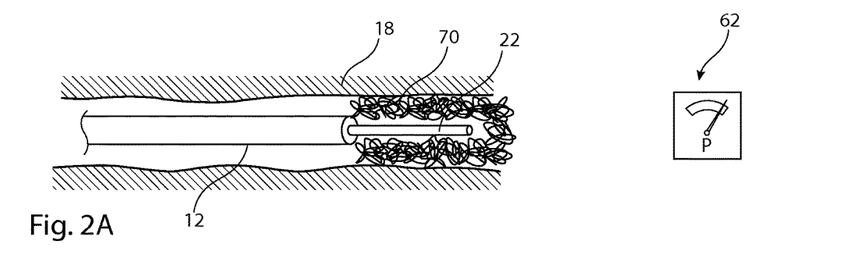
FIGS. 2A to 2D depict the RF ablation process of the preferred embodiment.

Referring first to FIG. 2A, once the electrode element 12 has been positioned at the desired location in the vessel 18, the control unit 40 commands the power unit 44 to supply RF energy to the electrode 12, as a result of which current passes from the exposed terminal tip 22 into the volume of the vessel 18, passing through the body of the patient to the cathode pad 14. The energy concentration at the electrode 22 causes local heating of blood and as a result coagulation of the blood to form a clot 70 around the exposed terminal tip 22. This phase of the operation of the apparatus 10 preferably occurs at first power level which is relatively high, indicated as such in the depiction of the meter display 62 in FIG. 2A.

The progress of ablation in this phase is preferably controlled by one or more sensors, for instance by means of a temperature probe 24 and temperature sensor unit 46 in the control unit 50 and/or by measuring the impedance of the circuit formed by the apparatus 10 when in operation. In practice, sensing temperature will aim to detect an increase in temperature indicative of passing a threshold at which blood will coagulate to form a clot 70, whereas measurement of impedance will determine when a sufficient amount of blood has clotted around the anode tip 22 to cause a drop in measured current and consequential increase in impedance.

It is not to be excluded that the control unit 50 could be operated without sensors, for example for a predetermined period of time at a predetermined energy which is considered sufficient to create a blood clot of the required dimensions. This is, though, not preferred as it is preferable to have as precise as possible an indication of the actual state of clotting of blood within the vessel 18 and therefore of the occlusion which is formed.

Figure 2B:
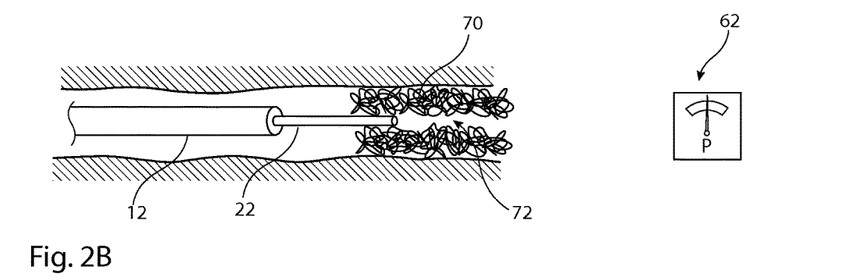

Referring now to FIG. 2B, at the end of the first phase of FIG. 2A, that is once a clot 70 is determined to have been formed in the vessel 18, the electrode element 12 is partially retracted, such that the anode tip 22 is at least partially exposed outside the blood clot 70. The withdrawal of the anode tip 22 will generally leave an aperture or lumen 72 within the blood clot 70. In the example shown in FIG. 2A, the anode tip 22 is only partially removed from within the volume of the blood clot 70, although in other embodiments the anode tip 22 may be fully retracted from the blood clot 70 so that the distal end of the anode tip 22 lies close to the blood clot 70 but not therewithin. In one example, a cathode tip of around 10 mm or so may be retracted by 2 to 10 mm at the end of the first phase of the process.

In this embodiment, during this second phase the control unit 50 commands the power unit 44 to apply energy at a second power level lower than the first power level applied during the phase of FIG. 2A. In some embodiments, during the retraction process, the control unit 50 may command the power unit 44 to apply no power at, that is until after the partial retraction of the anode tip 22.

It will be appreciated that the retraction of the anode tip 22, by means of retraction of the electrode element 12, may be effected manually by the medical practioner or automatically by means of a drive unit 50 provided in or coupled to the control unit 40. A suitable drive unit will be apparent to someone of average skill in the art.

Figure 2C:
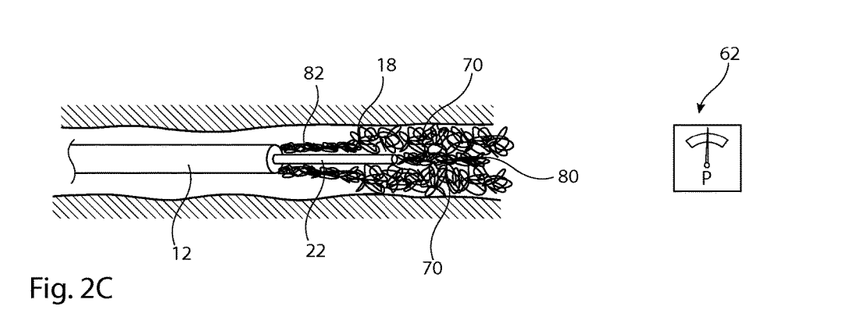

Referring now to FIG. 2C, during a subsequent phase of the RF ablation process, the control unit 40 commands the power unit 44 to apply energy at the second, lower, power level, which causes further ablation of blood within the vessel 18. In particular, this phase of operation of the apparatus 10 causes blood within the lumen 72 to coagulate and thereby form an additional blood clot 80 within the lumen 70 so as to close off the lumen 70, as well as further relatively minor blood coagulation around the exposed part of the anode tip 22 to form clotted blood 82 therearound. As the system is operated at a lower power level than the first power level, in this embodiment, the volume of the blood which is clotted is substantially less and preferably such as not to alter notably the length of the blood clot 70 produced in the first phase of the process shown in FIG. 2A. Therefore, the occluding barrier 70 preferably remains substantially the same length even in this second phase of RF ablation process. Specifically, the secondary blood clotting 82 is insufficient to fill the width of the vessel 18 and in practice will not obstruct any side vessels. The effective length of the blood clot will remain the length of the primary blood clot 70.

The degree of clotting during the second phase of the ablation process of FIG. 2C can again be sensed by the temperature probe 24 and temperature sensor unit 46 and/or by the impedance unit 48. It will be appreciated that the temperature reached during this second phase of and/or the impedance change may very well differ from those experienced during the first phase of the process, depicted in FIG. 2A. The person skilled in the art will be able to determine suitable thresholds for achieving such secondary clotting 80, 82.

The process of partial retraction and RF ablation at a lower power level depicted in FIG. 2C can be carried out a plurality of times during the process. In one example, the anode tip 22 may be retracted only a small distance from within the blood clot 70, the second phase carried out, the anode tip 22 retracted a little further, the second ablation phase operated again and so on, until it has been deemed that a sufficient secondary barrier 80 has been produced within the lumen 72 of the first formed blood clot 70. In other examples, the second phase may be carried only once.

Figure 2D:
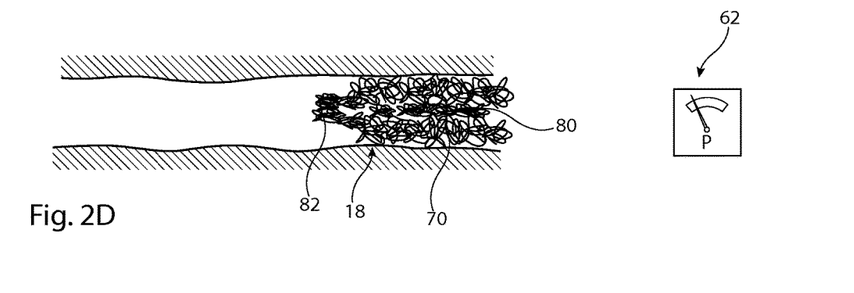

At the end of the second RF ablation phase, the electrode and consequently the anode tip 22 are completely retracted from the treatment site and the vessel 18, thereby to leave a blood clot formed of a first blood clot 70 and secondary blood clots 80, 82. At this stage the control unit 50 will have commanded the power unit 44 to cut all power to the electrodes 22, 14. As can be seen, there is produced a blood clot formation 70-82 which is completely sealed and which, moreover, is not unduly long.

Figure 3:
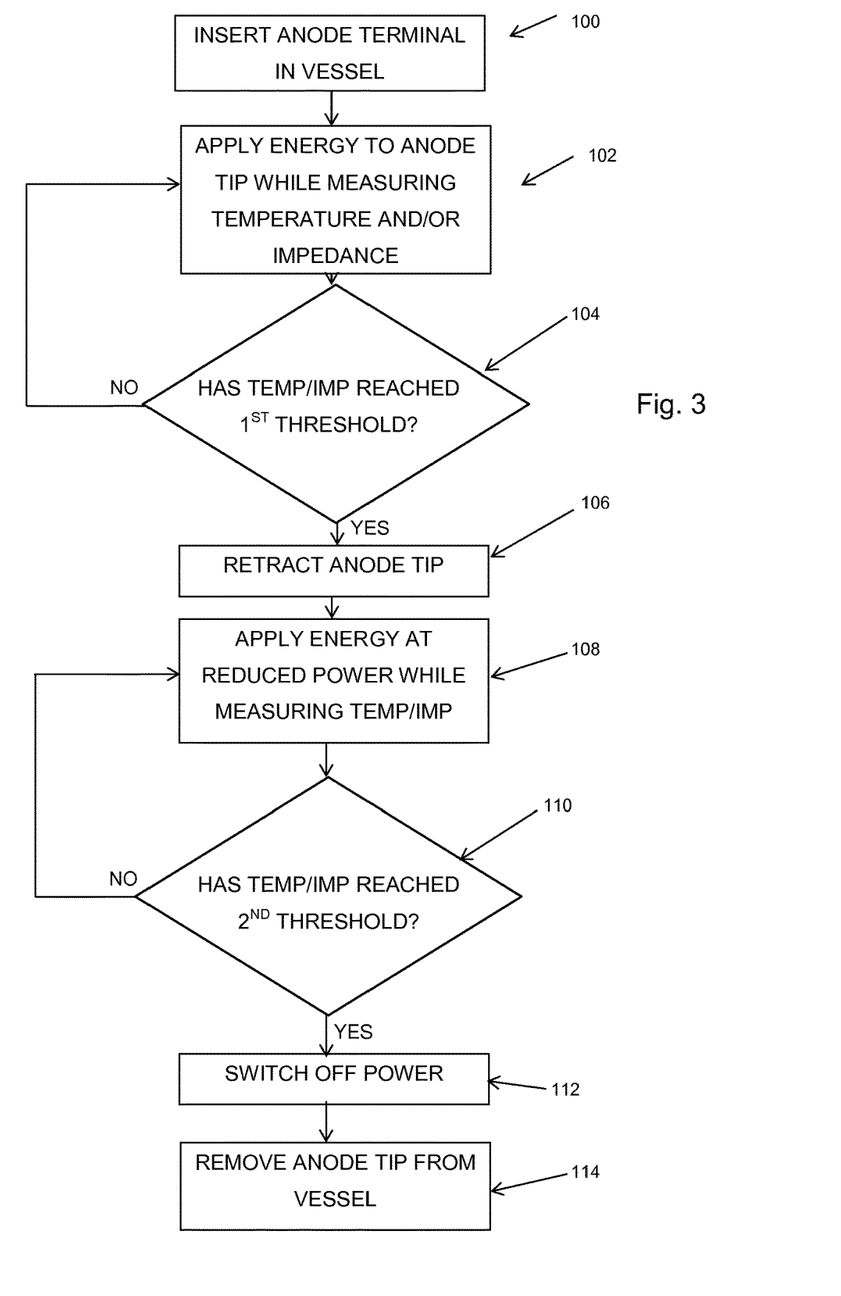
FIGS. 3 to 5 are flow charts depicting different functionalities of the control system and preferred steps of operating the apparatus.
Figure 4:
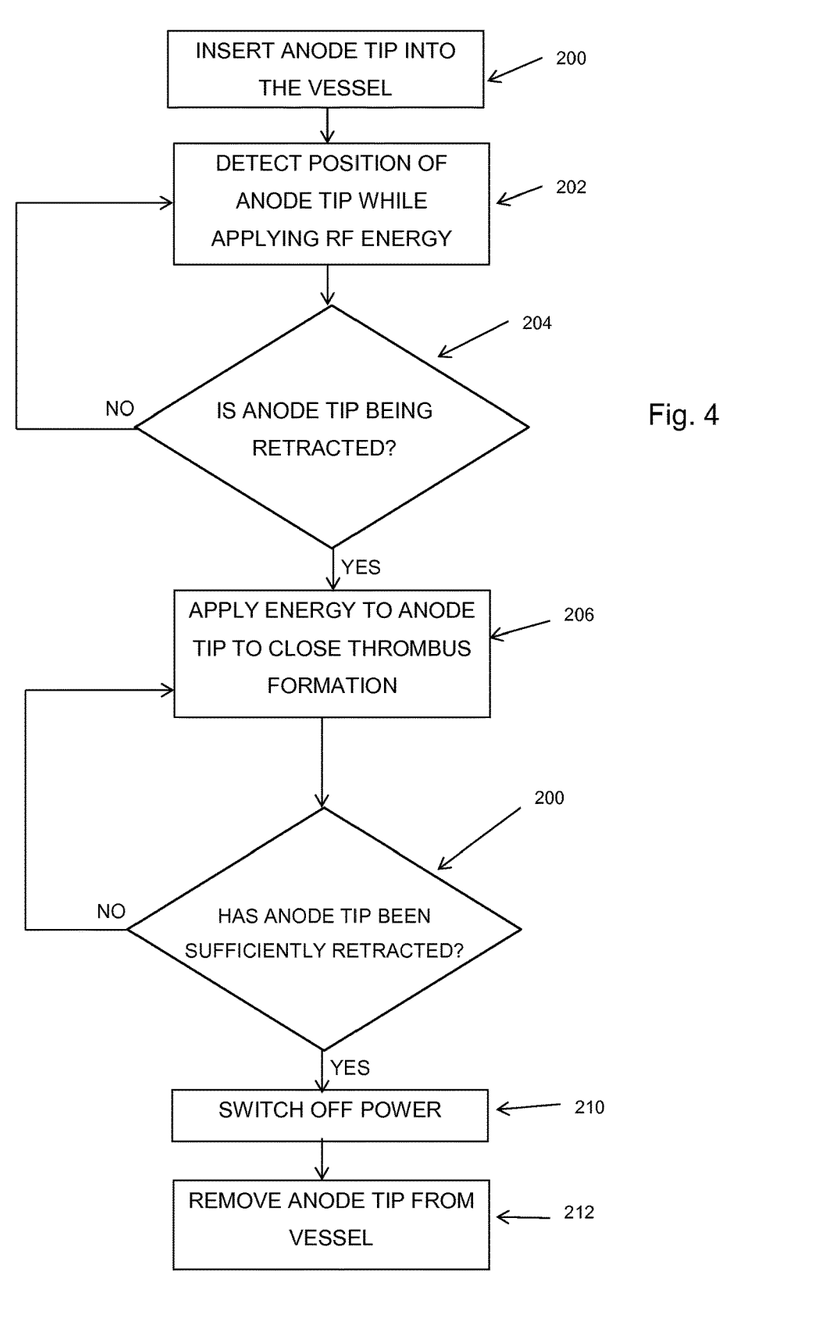
Figure 5:
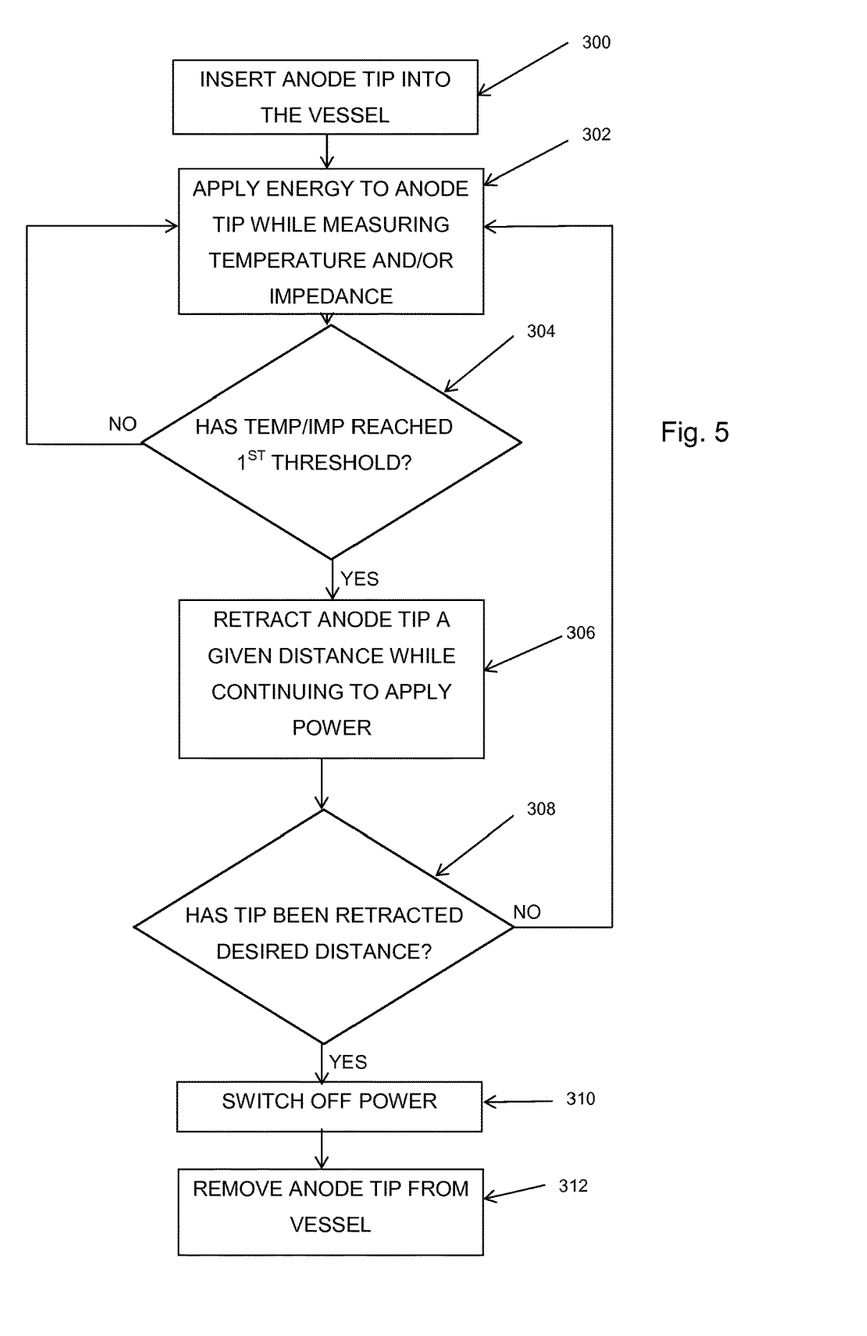

FIGS. 3 to 5 are flow charts depicting three different modes of operation of the apparatus 10 of FIG. 1, carried out by the control unit 40. The skilled person will appreciate that the apparatus 10 can be operated also in modes other than those described in connection with FIGS. 3 to 5. The skilled person will also appreciate that the control unit 40 may be set up to operate in a single mode of operation, but that in other embodiments may be programmed to operate in one of a plurality of modes of operation, as desired by the practitioner or required for the medical indication.

Referring first to FIG. 3, in this mode of operation, the electrode element 12 is, at step 100, inserted endoluminally into a patient's vessel up to the treatment site. Once positioned as necessary, at step 102, RF energy is applied to the anode tip 22 while measuring the temperature of the tip 22 and/or impedance through the circuit. At step 104, the control unit 40 and in particular the processing unit 42, by continuous monitoring of temperature and/or impedance, determines whether the temperature and/or impedance has reached a first threshold indicative of generation of blood clot 70. If the threshold has not been reached, the control unit 40 continues commanding the power unit 44 to apply energy to the anode tip at the first energy level. On the other hand, if at step 104 it is determined that the first threshold has been reached, the anode tip is retracted, either to remain partially within the clot formation 70 or to be fully withdrawn therefrom as described above, and the processing unit 42 then commands at step 108 the power unit 44 to apply RF energy to the anode tip 22 at reduced power, while continuing to measure temperature and/or impedance. The processing unit 44 continues monitoring the temperature and/or impedance at step 110 to determine therefrom whether this has reached a second threshold level. If the second threshold is deemed not to have been reached at step 110, the system continues operating in accordance with step 108, that is to apply energy at the reduced power level. On the other hand, if it is determined at step 110 that the second threshold has been reached, the processing unit 42 switches off power at step 112, on the basis that the condition at FIG. 2C is deemed to have been reached. At step 114, the electrode element 12 and therefore the anode tip, is removed from the vessel.

In the embodiment of FIG. 4, a different mode of operation is shown. At step 200, the electrode element 12, and therefore anode tip, are inserted endoluminally into the vessel, as in step 100 of the embodiment of FIG. 3. At step 202 the processing unit 42 detects the position of the anode tip within the vessel. If at step 204 it is determined that the anode tip is being retracted, operation proceeds to step 206. On the other hand, if it is not detected that the anode tip is being retracted, the process returns to step 202 to continue applying RF energy while continuing to monitor the position of the anode tip. When it is determined that the anode tip is being retracted, the process proceeds to step 206 at which energy continues to be applied to close the thrombus formation. This energy is in the preferred embodiment applied at the lower energy level in order to create secondary thrombus formations as shown in FIG. 2C. In other embodiments energy can be applied at the first power level or a power level sufficient to cause greater, that is larger, thrombus formation and further occlusion of the vessel.

The processing unit 42 continues to monitor the position of the anode tip 22 and when it is determined that it has been retracted by a predetermined distance deemed sufficient to close the thrombus formation 70, the processing unit 42 moves to step 210, at which it commands the power unit 44 to switch off power to the terminals 22. Then, at step 212, the electrode element 12 and therefore the anode tip 22 are removed from the vessel.

In its simplest form, the embodiment of FIG. 4 does not measure changes in temperature and/or impedance during the RF ablation process and the system continues applying RF energy where it is determined that the anode tip is being retracted. This embodiment, therefore, in its simplest form avoids leaving an open lumen 72 within the formed blood clot 70, which could as a result lead to incomplete occlusion of the vessel 18 and risk of recanalization. It is to be understood that the embodiment of FIG. 4 could also include steps to measure temperature and/or impedance and to determine whether these have reached the first and/or the second thresholds disclosed above in connection with the embodiment of FIG. 3.

Another embodiment of mode of operation of the apparatus 10 of FIG. 1 is shown in FIG. 5. In this embodiment, as in with the previous embodiments, at step 300 electrode element 12 and therefore anode tip 22 are introduced into the vessel to the location at which treatment is to be carried out.

At step 302 the control unit 42 commands the power unit 44 to apply RF energy to the anode tip 22, whilst at the same time measuring temperature and/or impedance at the anode tip 22. At step 304, the processing unit 42 determines whether the temperature and/or impedance has reached the first threshold and if it has not, step 302 continues to operate. On the other hand, when it is determined at step 304 that the first threshold has been reached, operation passes to step 306, at which the control unit commands retraction of the anode tip 22 by a given distance. This may be by operating the drive unit 50 shown in FIG. 1 or by displaying on a user interface a command instructing the user to effect the necessary withdrawal (the user can equally be warned by an acoustic and/or vibratory command). At step 308 the processing unit 42 determines whether the anode tip 22 has been retracted by a desired distance. This distance is deemed to be the desired total length of the occluding barrier formed by the blood clot 70. If it is deemed that the anode tip has not been retracted by the desired distance, the process returns to step 302 to continue applying RF energy. It is to be understood that in returning to step 302 a blood clot of the type shown in FIG. 2A will be generated, but more proximally, in effect to extend the length of the blood clot 70 to create a longer occluding barrier extending radially all the way to the vessel walls. Once, at step 308, it has been determined that the anode tip has been retracted by the desired distance, typically equivalent to the desired length of the blood clot 70, the process passes to step 310, at which power is switched off and then, at step 312, the electrode element 12 and anode tip 22 are removed from the patient.

It is to be understood that between steps 308 to 310, the control unit 40 and in particular the processing unit 42 may command a process equivalent to steps 108 and 110 in the embodiment of FIG. 3 in order to create a secondary occlusive barrier 80, 82 in order to close off any lumen in the formed blood clot 70. It is also to be understood that a phase of reduced power may be effected between steps 306 and 308 of the embodiment of FIG. 5, to create a progressive barrier 80 within the lumen 72 of the formed blood clot 70. In such an event, the embodiment of FIG. 5 will then apply power at a higher power level over a longer period of time in order, in effect, to grow the blood clot 82 at the exposed end of the anode tip 22 until the latter is deemed to have filled the volume of the vessel 18, that is grown into abutment with the vessel walls.

Thus, the embodiment of FIG. 5 can be used to create an occlusion of varying lengths as well as ensuring closure of the lumen left by the retracting anode tip 22.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. Apparatus for closing a blood vessel have a vessel wall, the apparatus comprising:
   an elongate electrode element for being passed endoluminally to a treatment site and having at least one electrical terminal at a distal end thereof;
   a power supply for supplying energy to the electrode element;
   a detection unit for detecting at least one operational change at the at least one electrical terminal; and
   a control unit connected to the power supply and to the detection unit; wherein the control unit is operable to control the power supply to supply energy to the electrode element at a first step at a first power level to heat blood within the blood vessel without ablating the vessel wall to cause a primary blood coagulation, the first power level being substantially constant during the first step,
   to detect at least one operational change at the at least one electrical terminal, and
   in a second step, to control the power supply after detecting the at least one operational change to supply energy to the electrode element at a second power level lower than the first power level to cause a secondary blood coagulation once the operational change has been detected, the second power level being substantially constant during the second step.

2. Apparatus according to claim 1, including a user notification unit coupled to the control unit, the control unit being operable to generate a notification on detection of the operational change in the at least one electrical terminal.

3. Apparatus according to claim 1, wherein the control unit is operable to command a partial retraction of the electrode element in a proximal direction on detection of the operational change.

4. Apparatus according to claim 3, including a positioning unit coupled to the control unit, the positioning unit being operable to effect said partial retraction of the electrode element in a proximal direction on detection of said operational change.

5. Apparatus according to claim 3, wherein the control unit is operable to generate a notification to effect said partial retraction of the electrode element.

6. Apparatus according to claim 1, including an electrode position sensor coupled to the control unit, wherein the control unit is operable to control the power supply to supply energy to the electrode element at the or a second power level lower than the first power level when partial retraction of the electrode element has been detected.

7. Apparatus according to claim 6, wherein the control unit is operable to command the power supply to supply power to the electrode element until the electrode element has been retracted by a predetermined distance.

8. Apparatus according to claim 7, wherein the predetermined distance is equivalent to a desired length of closure of the vessel.

9. Apparatus according to claim 1, wherein the operational change includes at least one of: change in measured impedance and change in temperature.

10. Apparatus according to claim 9, including a temperature sensor at the distal end of the electrode element.

11. Apparatus according to claim 1, wherein the electrode element includes an anode terminal, the apparatus including a cathode pad; or the electrode element includes anode and cathode terminals.

12. Apparatus for closing a blood vessel have a vessel wall, the apparatus comprising:
    an elongate electrode element having at least one electrical terminal at a distal end thereof;
    a power supply for supplying energy to the electrode element;
    a detection unit for detecting at least one operational change at the at least one electrical terminal;
    a position sensor arranged to detect the position of the distal end of the electrode in a patient;
    a control unit connected to the power supply, to the detection unit and to the position sensor; wherein the control unit is operable to control the power supply to supply energy to the electrode element at a first step at a first power level to heat blood within the blood vessel without ablating the vessel wall, the first power level being substantially constant during the first step,
    to determine movement of the electrode and to apply power to the electrode when the electrode has been deemed to have been moved by a first predetermined distance, and
    in a second step, to supply energy to the electrode element after detecting the at least one operational change at a second power level lower than the first power level once the electrode has been deemed to have been moved by the first predetermined distance and the operational change has been detected, the second power level being substantially constant during the second step.

13. Apparatus according to claim 12, wherein the control unit is operable to apply power to the electrical terminal continuously when in an initial position and while the electrode element is moved by the predetermined distance; or wherein the control unit is operable to apply power to the electrical terminal discontinuously, when in an initial position and after the electrode element has been moved by the predetermined distance.

14. Apparatus according to claim 12, wherein the control unit is operable to apply power to the electrical terminal up to a second distance greater than the first predetermined distance.

15. Apparatus according to claim 14, wherein the second distance is equivalent to a desired length of closure of the vessel.

16. Apparatus according to claim 12, wherein the electrical terminal has a conductive length and the first predetermined distance is less than said conductive length.

17. Apparatus according to claim 12, including a positioning unit coupled to the control unit, the positioning unit being operable to move the electrode element in at least a proximal direction.

18. A method of closing a blood vessel having a vessel wall by means of apparatus including an elongate electrode element for being passed endoluminally to a treatment site and having at least one electrical terminal at a distal end thereof and a power supply for supplying energy to the electrode element; the method including the steps of:
    supplying energy to the electrode element at a first step at a first power level to heat blood within the blood vessel without ablating the vessel wall to cause a primary blood coagulation, the first power level being substantially constant during the first step;
    detecting at least one operational change at the at least one electrical terminal; and
    when said operational change has been detected, in a second step, supplying energy to the electrode element at a second power level lower than the first power level to cause a secondary blood coagulation, the second power level being substantially constant during the second step.

19. A method according to claim 18, including the step of generating a user notification on detection of the operational change in the at least one electrical terminal.

20. A method according to claim 18, including the step of partially retracting the electrode element in a proximal direction on detection of the operational change.

21. A method according to claim 20, including the step of detecting partial retraction of the electrode element.

22. A method according to claim 20, wherein the electrode element is retracted by a predetermined distance while supplying power thereto.

23. A method according to claim 22, wherein the predetermined distance is equivalent to a desired length of closure of the vessel.

24. A method according to claim 18, wherein the operational change includes at least one of: change in measured impedance and change in temperature.

* * * * *